United States Patent [19]

Togo et al.

[11] 4,072,687
[45] Feb. 7, 1978

[54] PROCESS FOR PRODUCING 2-AMINO-(2)-THIAZOLINE-4-CARBOXYLIC ACID

[75] Inventors: Kazushi Togo, Yokohama; Fumihide Tamura, Kawasaki; Naohiko Yasuda, Yokosuka; Takehiko Ichikawa, Fujisawa; Konosuke Sano, Machida; Keizo Matsuda, Kawasaki; Koji Mitsugi, Yokohama, all of Japan

[73] Assignee: Ajinomoto Co., Inc., Tokyo, Japan

[21] Appl. No.: 737,781

[22] Filed: Nov. 1, 1976

[30] Foreign Application Priority Data

Nov. 6, 1975 Japan .................................. 50-133372
Dec. 16, 1975 Japan .................................. 50-149998
Mar. 19, 1976 Japan .................................. 51-30537

[51] Int. Cl.² ............................................. C07D 277/18
[52] U.S. Cl. ........................... 260/306.7 T; 260/534 S; 260/564 R; 560/147; 560/213
[58] Field of Search ................................. 260/306.7 T

[56] References Cited

PUBLICATIONS

Behringer et al., Ann., 574, 140–156 (1951).

*Primary Examiner*—R. J. Gallagher
*Attorney, Agent, or Firm*—Oblon, Fisher, Spivak, McClelland & Maier

[57] ABSTRACT

2-Amino-(2)-thiazoline-4-carboxylic acid is prepared by dehydrochlorinating S-(β-carboxy-β-chloroethyl) isothiourea by adding it to an aqueous medium maintained at a pH ranging from 5.5 to 7.5 with an alkali.

7 Claims, No Drawings

PROCESS FOR PRODUCING 2-AMINO-(2)-THIAZOLINE-4-CARBOXYLIC ACID

BACKGROUND OF THE INVENTION

Field of the Invention

This invention relates to a process for producing 2-amino-(2)-thiazoline-4-carboxylic acid, hereinafter referred to briefly as "ATC".

SUMMARY OF THE INVENTION

An object of this invention is to provide a process for producing ATC inexpensively and in high yield. Other objects will become apparent from the following disclosure.

One embodiment of this invention, hereinafter referred to as Embodiment I, relates to a process for producing ATC comprising the addition of S-($\beta$-carboxy-$\beta$-chloroethyl) isothiourea, or a salt thereof, hereinafter referred to as "CIU", to an aqueous medium maintained a pH of 7.5 or less, preferably at a pH of from 7.5 to 5.5, using alkali. In this process, CIU is subjected to dehydrochlorination and ATC is produced by the resultant cyclization of CIU, as follows:

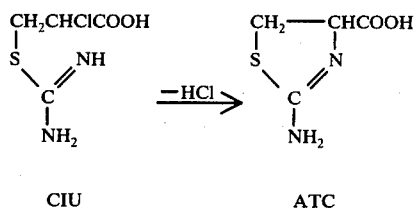

CIU           ATC

DESCRIPTION OF THE PREFERRED EMBODIMENTS

ATC has a known utility as an intermediate for synthesis of DL-cystine or its reduced form, DL-cysteine. Moreover, it is expected to have uses in the pharmaceutical field, for example.

Processes for producing L-cystine or L-cysteine, both of which are naturally occurring isomers, from ATC are not commercially practical if they comprise a step of optical resolution of a racemic mixture into the isomers, because such an optical resolution is very difficult to perform.

However, an enzymatic method of producing L-cystine or L-cysteine has recently been developed in which ATC is almost quantitatively converted as a substrate into L-cystine or L-cysteine using an asymmetric hydrolase. (See U.S. Pat. No. 4,006,057). The following experiment is illustrative of the enzymatic method.

EXPERIMENT 50 ml of an aqueous culture medium containing, per deciliter, 1 g of glycerol, 0.5 g of yeast extract, 0.5 g of peptone, 0.5 g of bouillon, 0.5 g of NaCl and 0.2 g of DL-ATC.3H$_2$O, which was adjusted to a pH of 7, was placed in a 500 ml flask, inoculated with Sarcina lutea ATCC 272, and held at 30° C for 16 hours with shaking.

Cells in the culture broth were collected by centrifuging, and freeze-dried. 30 g of the freeze-dried cells were suspended in 1 liter of an aqueous substrate solution containing, per deciliter, 1 g of DL-ATC.3H$_2$O, 1 g of KH$_2$PO$_4$ and 0.14 g of NH$_2$OH.HCl which was adjusted to pH of 8. The reaction mixture was maintained at 30° C for 53 hours.

Subsequently, 6 N NaOH was added to the reaction mixture to dissolve the precipitates formed. The reaction mixture was then subjected to centrifugation.

Using a very small portion of the supernatant liquid obtained by centrifuging, L-cystine and L-cysteine were determined by the bio-assay method, using Leuconostoc citrovorum ATCC 8081. This strain corresponds to both L-cystine and L-cysteine. Therefore, when both isomers are determined by this bio-assay method, the total amount of both isomers is obtained. The result revealed an accumulation of 5.1 mg of L-cystine and L-cysteine in a 1 ml reaction mixture, i.e., an 84% molar yield based on ATC.

The remaining supernatant liquid was added to 5 g of active carbon, heated and filtered. The amount of filtrate was 990 ml. After aerating overnight to convert the L-cysteine to L-cystine, the filter was concentrated under reduced pressure to crystallize the L-cystine.

The L-cystine crystals formed were filtered, washed with water and dried. The dried crystals weighed 3.8 g, a 75% yield based on the amount of L-cystine and L-cysteine formed in the reaction mixture.

This enzymatic method not only dispenses with the step of optical resolution, but also involves no pollution problems compared with the hydrolysis method commercially employed today in which human hair or the like is hydrolyzed and the L-isomers are separated from the hydrolyzate. According, it is reasonably supposed that the enzymatic method will replace such the hydrolysis method.

According to this invention, ATC, the substrate used in the above-mentioned commercially advantageous enzymatic method, may be easily produced inexpensively and in high yields.

H. Behringer reported a synthetic method of preparing ATC in Ann. 574,140 (1951). Methyl $\alpha$-chloroacrylate is added to thiourea and then hydrolyzed. After separation from the reaction mixture and suspension in water, the resultant CIU is treated with sodium hydroxide, aqueous ammonia or sodium hydrogencarbonate to give ATC in a 70% yield. No further particulars are reported. The inventors have made a thorough study of the resistivities of CIU and ATC to heat, acids and bases, and have found that both compounds are, when heated under alkaline conditions, i.e., in a pH range above about 7.8, considerably susceptible to decomposition. This decomposition remarkably increases with an increase in pH.

It is known that dehydrochlorination usually proceeds smoothly under alkaline conditions. In connection with conversion of CIU to ATC, conventional dehydrochlorinations like Behringer's are also carried out under the same conditions.

The inventors have, however, found that this particular dehydrochlorination of CIU to ATC, when carried out under nearly neutral to acidic conditions, more exactly in the pH range below 7.5, gives remarkably increased yields, compared with those obtained when the reaction is carried out in the pH range above 7.8, as is evident from Table 1. This invention is based on these findings. The turning point in yield is actually somewhere between pH 7.5 and 7.8, but has not been specifically ascertained.

The results shown in Table 1 were obtained using the following procedure. 6 g of CIU is suspended in 100 ml of water. 4N Aqueous ammonia in an amount of 1.1 times the number of moles of CIU, is added dropwise at 60° C to the suspension, while the reaction mixture is maintained at the given pH. The molar yield of the resulting ATC based on the amount of CIU was determined by high-speed liquid chromatography, immediately after the addition was completed. Accordingly, reaction time equals the addition time.

The high yields obtained in accordance with this invention may be principally ascribed to the facts that the dehydrochlorination proceeds smoothly under the nearly neutral to acidic conditions, and that the starting material, CIU, is stable under the same conditions. These facts are new findings.

In carrying out the process of Embodiment I, CIU may be used in its free form or as a salt form such as an addition salt with hydrogen chloride or sulfuric acid. It is dissolved or suspended in an aqueous medium to be subjected to the dehydrochlorination reaction. The alkali used is not critical. Metal hydroxides such as sodium hydroxide and calcium hydroxide, metal carbonates such as sodium hydrogencarbonate, and ammonia are all employable.

The dehydrochlorination may be carried out in the pH range below 7.5, but preferably is carried out in the pH range of from 7.5 to 5.5 in consideration of the reaction time required to complete the reaction. The temperature may range between 50° C and 100° C, preferably between 50° C and 80° C. Above 80° C the decomposition of ATC occurs.

ATC resulting from the reaction may be separated as crystals from the reaction mixture by cooling of the mixture as is or after concentration.

EXAMPLE 1

18.3 g of CIU was added to 170 ml of water and the suspension was maintained at 60° C with stirring. When, while the pH of the reaction mixture was being maintained at 7.5, 27.5 ml of 4N aqueous ammonia had been added dropwise over a 25minute interval, the mixture became transparent.

The reaction mixture was analyzed by high-speed-liquid-chromatography which revealed a 91.5% molar yield of ATC based on the amount of CIU.

The reaction mixture was concentrated under reduced pressure to about half its original volume, and was maintained at 5° C for 10 hours. The crystals (DL-ATC.3H$_2$O) formed were separated by filtering, washed with water, and dried under reduced pressure at 80° C for 5 hours.

The dried crystals (DL-ATC) weighed 13.0 g, representing an 89.0% molar yield based on the amount of ATC formed in the reaction mixture. (M.p., 205° C.; Anal.: Calcd. for C$_4$H$_6$N$_2$O$_2$S: C, 32.87; H, 4.14; N, 19.17; S, 21.94.) Found: C, 32.55; H, 4.09; N, 18.93; S, 21.49.)

EXAMPLES 2 to 5

The results of Examples 2–5, carried out under similar conditions to Example 1, are listed in Table 2.

Another embodiment of this invention, Embodiment II, relates to an improvement in the process of Embodiment I, in which CIU is produced by reacting an alkyl α-chloroacrylate, hereinafter referred to as "ACA", with thiourea in water in the presence of a mineral acid. The CIU formed is then subjected to dehydrochlorination.

According to the H. Behringer reference mentioned hereinbefore, CIU is prepared as follows. An ACA is reacted with thiourea in an organic solvent, such as methanol or ethanol, containing hydrogen chloride, dioxane-water, or acetic acid. The resulting S-(β-carboalkoxy-β-chloroethyl) isothiourea, hereinafter referred to as "CAIU", is hydrolyzed to give CIU.

Studies of the reaction between methyl α-chloroacrylate, hereinafter referred to as "MCA", and thiourea, using methanol, one of the most common and commercially cheapest solvents, as a solvent have been made. As a result, it has been found that, under such reaction conditions, S-methylisothiourea, CH$_3$SCNH(NH$_2$), hereinafter referred to as "MIU", is formed in a considerable amount, i.e., in about a 10% yields as a by-product in addition to the main product of S-(β-carbomethoxy-β-chloroethyl) isothiourea, hereinafter referred to as "CMIU". This is evident from Table 3.

The results shown in Table 3 were obtained by the following procedure. 24.1 g of MCA and 15.2 g of thiourea were reacted with one another in 200 ml of solvent at 60° C for 5 hours. The reaction mixture was subjected to high-speed liquid chromatography in order to quantitatively determine the molar yields of the products based on the amount of MCA.

The formation of the undesired MIU may be ascribed to the reaction between methanol as a solvent and thiourea, as follows.

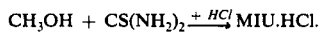

In turn, MIU, when treated with an alkali such as sodium hydroxide, gives methyl mercaptan, a notoriously evil-smelling compound. This means that the reaction mixture resulting from the reaction between an ACA and thiourea in methanol in the presence of mineral acid will, when treated with an alkali produce methyl mercaptan, having a notoriously evil smell. The alkali addition is made so that the S-(β-carboalkoxy-β-chloroethyl) isothiourea, hereinafter referred to as "CAIU", contained in the reaction mixture will be hydrolyzed and dehydrochlorinated to obtain ATC. From this point of view, CAIU is preferably treated with an alkali after being separated from the reaction mixture.

Furthermore, the reaction between an ACA and thiourea, when carried out in an organic solvent such as methanol or acetic acid, produces the corresponding CAIU as a main product. In order for CAIU to be hydrolyzed to CIU, previous isolation of the CAIU, or previous removal of the solvent from the reaction mixture is indispensable. This involves complicated manipulations.

In the past, mixtures of water with organic solvents, such as water-methanol and water-dioxane, have been studied as solvents for the reaction between an ACA and thiourea, but water alone has never been studied. It has been expected that an ACA such as methyl or ethyl α-chloroacrylate will react with thiourea in water proceed only slowly because of the sparing solubility of an ACA in water. It has been believed that because of the instability of an ACA, such a slow reaction would cause side reactions such as the polymerization of ACA and addition of HCl to ACA to occur. As a result, it was expected that low yields of the desired products CAIU and/or CIU would ensure water has not been used as solvent in the prior art possibly because of these preconceptions.

It has now been discovered that the above preconceptions are false. Embodiment II is the result. All the above-mentioned defects involved in the reaction between an ACA and thiourea using an organic solvent or its mixture with water may be avoided using this Embodiment.

In carrying out the process of this Embodiment, suitable ACA's include the methyl and ethyl esters. When hydrochloric acid is employed as the mineral acid, it is used in an amount, 1 - 5 times the equivalent amount of the thiourea.

The ACA is added to an aqueous solution containing thiourea and HCl. The mixture is maintained at a temperature of 50° C to 100° C with stirring. At a temperature below 50° C the reaction time required is long; and above 100° C a decomposition reaction occurs.

This addition reaction between an ACA and thiourea requires a reaction time from about 30 min. to about 5 hours, depending on the reaction temperature. Hydrolysis of the addition product CAIU to CIU requires an additional period of heating at the same temperature of about 1 to 2 hours. The hydrolysis can be accelerated by removal of the alcohol which results from the hydrolysis by concentrating the reaction mixture, for example.

The CIU formed may be separated as crystals from the reaction mixture by neutralizing the mixture with an alkali such as NaOH or NH$_4$OH.

Of course, CIU may be separated from the reaction mixture before being subjected to the subsequent step of cyclization to ATC. However, the CIU, formed may be subjected to the subsequent step, contained in the reaction mixture, i.e., without being separated therefrom. Apparently, some of the advantages of Embodiment II are better realized in the latter case. These include a reduced amount of acid: simplified manipulation e.g., no recovery of the reaction solvent or separation of the intermediates required; high yield of ATC separated from the reaction mixture; reduced waste waters and the like.

EXAMPLES 6 and 7

24.1 g (0.2 mole) of MCA and 15.2 g (0.2 mole) of thiourea were added to 400 ml of 4N HCl and the mixture was maintained at 80° C with stirring for 4 hours.

The reaction mixture was adjusted to a pH of 5.0 with 2N NH$_4$OH, and a temperature below 10° C to crystallize CIU. The crystals were separated by filtration and dried under a reduced pressure at 60° C.

The dried crystals weighed 31.1 g which was an 85.1% molar yield based on MCA. Its properties are: m.p., 178° C (decomposition); Anal: Calcd. for C$_4$H$_7$N$_2$O$_2$ClS: C, 26.30; H, 3.90; N, 15.30; Cl, 19.40; S, 17.60; Found: C, 26.38; H, 3.84; N, 15.27; Cl, 19.69; S, 17.40.

The mother liquor from which the CIU crystals had been separated gave off no mercaptan smell.

Another 24.1 g of MCA and 15.2 g of thiourea were added to 400 ml of 1 N HCl. The mixture was maintained at 90° C with stirring for 1 hour. At this time, the reaction mixture was high-speed-liquid-chromatographed. This revealed that CMIU and CIU were formed in molar yields of 14.0% and 76.0% respectively, both based on MCA.

The reaction mixture was added to 200 ml of 2N HCl and maintained at 80° C with stirring for an additional 2 hours. The reaction mixture was again high-speed-liquid-chromatographed, which revealed a trace of CMIU and an 88.0% yield of CIU.

The CIU was separated in the same way as above.

The two CIU products were successfully subjected to dehydrochlorination to give ATC.

EXAMPLE 8

26.9 g (0.2 mole) of ethyl α-chloroacrylate, hereinafter referred to as "ECA", and 15.2 g (0.2 mole) of thiourea were added to 400 ml of 0.75N HCl and the mixture was maintained at 60° C with stirring for 4 hours. At this time, CIU and S-(β-carboethoxy-β-chloroethyl) isothiourea, hereinafter referred to as "CEIU", were formed in the reaction mixture in yields of 73.8% and 17.0% respectively.

The reaction mixture was added to 200 ml of 4N HCl and maintained at 80° C to stirring for an additional 2 hours. This time, the reaction mixture contained almost no CEIU, and contained CIU in a 88.3% yield.

While being maintained at a pH of 6.5 with stirring, 4N NH$_4$OH was added to the last-mentioned reaction mixture at 65° C, over a forty-five minute interval. The reaction mixture became transparent after the interval and the addition was discontinued. High-speed-liquid chromatography revealed that ATC was formed in the reaction mixture in a 78.6% yield based on ECA.

The dried ATC crystals, separated from the reaction mixture in the same way as in Example 1, weighed 21.9 g representing a 74.9% molar yield based on CIU.

EXAMPLE 9

24.1 g of MCA and 15.2 g of thiourea were added to 800 ml of 0.5N HCl. The mixture was maintained at 70° C with stirring for 5 hours. CIU was formed in the reaction mixture in a 85% molar yield based on MCA.

2N NaOH was added dropwise to the reaction mixture maintained at a pH of 5.8 with stirring, and a temperature of 65° C. The reaction mixture became transparent after a thirty-minute addition. ATC was formed in the reaction mixture in 73.5% molar yield based on MCA.

The dried ATC crystals separated from the reaction mixture as in Example 1 weighed 20.5 g in which represented a 70.0% molar yield based on CIU.

A further embodiment of this invention, hereinafter referred to as Embodiment III, relates to a further improvement of Embodiment II and, accordingly, Embodiment I. For this embodiment, an ACA is produced by treating an alkyl α,β-dichloropropionate, hereinafter referred to as "ACP", in water with an alkali. The ACA formed is subjected to the addition reaction with thiourea.

According to the prior art, dehydrochlorination of an ACP to the corresponding ACA is carried out in an alcohol solvent or without any reaction solvent using a dehydrochlorinating agent such as sodium acetate, a sodium phosphate, or an alkali metal alcoholate. Alkalis, such as metal hydroxides e.g., NaOH or Ca(OH)$_2$, and carbonates, e.g., Na$_2$CO$_3$ or NaHCO$_3$ have never been used as the dehydrochlorinating agent. The expectation probably has been that such alkalis would accelerate hydrolysis of ACP or ACA and polymerization of ACA. Moreover, water has never been used as the reaction solvent, probably because of the expectations that dehydrochlorination of an ACP would proceed slowly due to its sparing solubility and that such a slow dehydrochlorination will in turn cause polymerization of the resulting ACA.

It has now been found that the above preconceptions are false, as is evident from Table 4, for example, Embodiment III is based upon this discovery.

The results shown in Table 4 were obtained by the following procedure. To 15.7 g (0.1 mole) of methyl α,β-dichloropropionate, herein referred to as MCP, was added 6.0 g (0.15 mole) of NaOH. The reaction mixture was maintained with stirring at the temperature shown for the time shown. The reaction mixture was gas-chromatographed to determine quantitatively the amount of MCP remaining and MCA produced. The control run was carried out using no reaction solvent.

According to this Embodiment, the dehydrochlorination reaction proceeds smoothly irrespective of the heterogeneous reaction system involved. ACA is produced quantitatively with no formation of the by-products resulting from hydrolysis or polymerization.

In carrying out the process of Embodiment III, the ACP is preferably a lower alkyl ester such as the methyl, ethyl, propyl or butyl ester. The dehydrochlorinating agent is not very critical, but the alkalis mentioned above with reference to conventional knowledge can be used.

The latter should be used in an amount more than the equivalent amount of ACP and preferably in a concentration below 12N. A higher concentration is prone to accelerate the polymerization of the resulting ACA.

The dehydrochlorination reaction is preferably carried out with stirring, because of the heterogeneous reaction system. The reaction temperature may range from 0° C to 90° C, and preferably is between 10° C and 40° C. In the latter range, side reactions are suppressed and the desired product is produced in high yield.

Of course, the ACA formed may be subjected to the subsequent step after being separated from the reaction mixture. However, when the ACA is subjected to the subsequent step, without being separated from the reaction mixture the same advantages mentioned above in connection with Embodiment II are better realized. The process of this embodiment produces ATC in very high overall molar yields, as high as 70% to 75% when carried out with no intermediates separated from the reaction mixtures.

EXAMPLE 10

78.5 g of MCP was added dropwise with stirring to 200 ml of 4N NaOH, while the temperature was being maintained below 50° C. After an hour's stirring, the MCA layer was separated from the aqueous layer and concentrated under reduced pressure (50 mm Hg, 65° C to 80° C) to give 51 g of residue.

The residue was identified as MCA by nuclear magnetic resonance and elemental analysis. (Anal. Calcd: for $C_4H_5O_2Cl$: C, 39.86%; H, 4.18%; Cl, 29.41%; Found: C, 39.92%; H, 4.09%; Cl, 29.10%.)

The MCA was successfully subjected to the subsequent reactions to give ATC.

EXAMPLE 11

157 g (1 mole) of MCP was added dropwise with stirring to 400 ml of 4N NaOH, while the temperature was being maintained below 30° C.

The reaction mixture was after then stirred for an hour and gas-chromatographed to reveal that MCA had been formed almost quantitatively, i.e., in a 99.3% molar yield based on MCP.

Without having been separated from the reaction mixture, the MCA was added to 76 g (1 mole) of thiourea and 250 ml 35% of HCl. The mixture was maintained at 70° C with stirring for 2 hours and then concentrated to two thirds of its original volume to remove the methanol. The concentrate was then added to 300 ml of water maintained at 70° C for 2 hours to hydrolyze the CMIU. It was then high-speed-liquid-chromatographed to reveal that CIU had formed in a 90.5% molar yield based on MCP.

The reaction mixture, while being maintained at 70° C, was adjusted to a pH of 5.0 NaOH. It was then added with 91 g of $NaHCO_3$, while the pH was maintained below 7.5. It was after then maintained at 70° C for an additional 30 minutes cooled to 5° C and left for 12 hours.

The resulting crystals were then separated by filtering, dried at 60° C and weighed 108.9 g. M.P. 205° C. Anal. Calcd. for $C_4H_6N_2O_2S$: given hereinbefore in Example 1. Found: C, 32.63; H, 4.10; N, 18.91; S, 21.56. They were identified as ATC.

EXAMPLE 12

157 g (1 mole) of MCP was added dropwise with stirring to 250 ml 4N NaOH, while the temperature was being maintained below 50° C. After thirty-minutes of stirring, MCA was formed in a 97.5% molar yield.

The mixture was then added with to 76 g (1 mole) of thiourea and 120 ml of 35% HCl maintained at 80° C for 7 hours. CIU was formed in an 89.0% molar yield.

The reaction mixture was then cooled to 60° C, adjusted to a pH of 7.0 with 4N NaOH, while being maintained at the temperature. 250 ml of 4N $NH_4OH$ was then added, while the pH was maintained below 7.5. It was then maintained at 60° C for an additional 30 minutes, cooled to 5° C and left for 12 hours.

The resulting crystals were separated by filtering and dried to give 106.7 g of ATC.

TABLE 1

| Run No. | pH | reaction time (min.) | ATC yield (%) |
| --- | --- | --- | --- |
| 1 | 10.0 | 5 | 33.5 |
| 2 | 8.5 | 5 | 44.2 |
| 3 | 7.8 | 10 | 58.5 |
| 4 | 7.5 | 15 | 82.3 |
| 5 | 7.0 | 15 | 83.4 |
| 6 | 6.8 | 30 | 89.8 |
| 7 | 6.4 | 35 | 91.2 |
| 8 | 6.0 | 70 | 89.3 |
| 9 | 5.5 | 120 | 88.8 |

TABLE 2

| Conditions & Yields | Example | | | |
| --- | --- | --- | --- | --- |
| | 2 | 3 | 4 | 5 |
| Reaction conditions | | | | |
| CIU | 18.3g | 18.3g | 18.3g | 22.0g (hydrochloride) |
| Water | 350ml | 150ml | 180ml | 140ml |
| Temperature | 65° C | 80° C | 55° C | 65° C |
| pH | 5.8 | 7.0 | 7.5 | <6.5 |
| Alkali | 2N NaOH | 2M $Na_2CO_3$ | $NaHCO_3$ (powder) | 4N $NH_4OH$ |

TABLE 2-continued

| Conditions | Example | | | |
| --- | --- | --- | --- | --- |
| & Yields | 2 | 3 | 4 | 5 |
| Interval | 57.5ml 65min. | 28.7ml 35min. | 9.24g 60min. | 52.5ml 60min. |
| Yields based on CIU | | | | |
| ATC formed in the reaction mixture | 88.5% | 89.2% | 88.3% | 91.0% |
| ATC separated as crystals | 12.57g (86.1%) | 12.53g (85.8%) | 12.59g (86.2%) | 12.92g (88.5%) |

TABLE 3

| Run No. | Solvent | HCl to thiourea (mole ratio) | Yield (%) | | |
| --- | --- | --- | --- | --- | --- |
| | | | CMIU | CIU | MIU |
| 1 | methanol | 1.0 | 75.2 | trace | 13.4 |
| 2 | methanol | 2.5 | 86.2 | trace | 12.8 |
| 3 | methanol—water(9/1)* | 1.0 | 60.3 | 11.8 | 10.9 |
| 4 | methanol—water(8/2)* | 1.5 | 64.3 | 19.7 | 10.8 |
| 5 | methanol—water(7/3)* | 2.9 | 64.7 | 25.3 | 10.2 |
| 6 | water | 2.0 | 14.3 | 75.0 | 0 |

*volume/volume ratio

TABLE 4

| Run No. | Reaction | | Analytical Results | |
| --- | --- | --- | --- | --- |
| | Temperature(° C) | Time(min.) | MCP(%) | MCA(%) |
| 1 | 0 | 30 | 15.5 | 84.7 |
| 2 | 30 | 30 | 0 | 98.5 |
| 3 | 30 | 60 | 0 | 99.4 |
| 4 | 50 | 30 | 0 | 97.8 |
| 5 | 90 | 30 | 0 | 75.0* |
| control | 90 | 30 | 92.5 | 6.7 |

*Besides MCA, a polymer-like white solid was precipitated.

What is claimed as new and intended to be covered by Letters Patent is:

1. A process for producing 2-amino-(2)-thiazoline-4-carboxylic acid which comprises dehydrochlorinating S-($\beta$-carboxy-$\beta$-chloroethyl) isothiourea by adding it to an aqueous medium maintained at a pH ranging from 5.5 to 7.5 with an alkali.

2. The process of claim 1 wherein the temperature during the dehydrochlorination is 50° – 80° C.

3. A process for producing 2-amino-(2)-thiazoline-4-carboxylic acid, which comprises:

preparing an alkyl $\alpha$-chloracrylate by dehydrochlorinating an alkyl $\alpha$, $\beta$-dichloropropionate in water in the presence of an alkali;

preparing a S-($\beta$-carboxy-$\beta$-chloroethyl) isothiourea by reacting said alkyl $\alpha$-chloroacrylate with thiourea in water in the presence of a mineral acid; and dehydrochlorinating said S-($\beta$-carboxy-$\beta$-chloroethyl) isothiourea by adding said S-($\beta$-carboxy-$\beta$-chloroethyl) isothiourea to an aqueous medium maintained at a pH ranging from 5.5 to 7.5 with an alkali.

4. The process of claim 3, wherein said isothiourea is used in the subsequent dehydrochlorinating step without being separated from the reaction mixture.

5. The process of claim 3, wherein the temperature of said isothiourea formation step is 50° to 100° C.

6. The process of claim 3 wherein said alkyl $\alpha$-chloroacrylate is used in the subsequent isothiourea formation step without being separated from the reaction mixture.

7. The process of claim 3 wherein the temperature of said alkyl $\alpha$-chloroacrylate formation step is 0° to 90° C.